United States Patent [19] [11] 4,365,376
Oda et al. [45] Dec. 28, 1982

[54] MOUTH CLEANING DEVICE

[75] Inventors: Takeshi Oda; Toshio Tanabe; Yoshimasa Tanaka, all of Kadoma, Japan

[73] Assignee: Matsushita Electric Works, Ltd., Osaka, Japan

[21] Appl. No.: 217,002

[22] PCT Filed: Mar. 13, 1980

[86] PCT No.: PCT/JP80/00043
§ 371 Date: Nov. 14, 1980
§ 102(e) Date: Nov. 14, 1980

[87] PCT Pub. No.: WO80/01873
PCT Pub. Date: Sep. 18, 1980

[30] Foreign Application Priority Data

Mar. 15, 1979 [JP] Japan ................................. 54-30855

[51] Int. Cl.³ ............................................. A46B 13/06
[52] U.S. Cl. ................................... 15/22 R; 128/62 A
[58] Field of Search .................. 15/22 R, 22 A, 22 C; 310/50; 128/62 A

[56] References Cited

U.S. PATENT DOCUMENTS 3,465,751  9/1969  Powers ........................... 15/22 R X
3,536,065 10/1970  Moret ............................ 15/22 R X
4,146,020  3/1979  Moret et al. .................... 15/22 R X

FOREIGN PATENT DOCUMENTS 2109006 10/1971 Fed. Rep. of Germany ... 128/62 A
2019003 11/1971 Fed. Rep. of Germany ..... 15/22 R
2544535  4/1977 Fed. Rep. of Germany ... 128/62 A
43-27714 11/1968 Japan .
46-16548  5/1971 Japan .

Primary Examiner—Edward L. Roberts
Attorney, Agent, or Firm—Burns, Doane, Swecker & Mathis

[57] ABSTRACT

A mouth cleaning device of this invention comprises a hand held gripping part with brush and nozzle members selectively mounted thereto. The gripping part is provided with a driving rod for transmitting to the selectively mounted brush member a reciprocal turning force and for providing to the selectively mounted nozzle member a water feeding path to lead water to the nozzle member from an external water feeding means. A driving means provides a reciprocal turning force to the driving rod. A change-over switch drives the driving means only when the brush member is mounted so that, when the brush member is mounted to the gripping part, the brush member will be reciprocally turned to perform tooth brushing. When the nozzle member is mounted to the gripping part, water will be jetted out of the nozzle member to perform gum cleaning and massaging.

6 Claims, 24 Drawing Figures

MOUTH CLEANING DEVICE

TECHNICAL FIELD OF THE INVENTION

This invention relates to mouth cleaning devices and, more particularly, to a mouth cleaning device which allows one to selectively perform tooth brushing or gum cleaning by mounting either a brush member or nozzle member to a single main body.

BACKGROUND OF THE INVENTION

While one may cleanse one's mouth by tooth brushing and gum cleaning one has been unable to perform both tooth brushing and gum cleaning simultaneously unless respective equipment for both are provided. Conventionally, they have been prepared separately for reasons that an integral combination of the tooth brushing and gum cleaning equipment has rendered the device bulky, to deteriorate with usage and so on.

With a view to solving this problem, a personal mouth cleaning device has been suggested in a Japanese Patent Publication No. 16548/1971 wherein the same main body is used with the brush member and nozzle member interchanged with each other. The above-mentioned device however, employs an hydraulically operated motor as a driving source for the brush member which motor is defective in that the brush member will not operate when the liquid is exhausted or its amount is reduced.

OBJECTS OF THE INVENTION

A first object of the present invention is, therefore, to provide a mouth cleaning device wherein a hand held gripping part of the mouth cleaning device is reduced in size.

A second object of the present invention is to provide a mouth cleaning device wherein a brush member and nozzle member are made interchangeable with each other with respect to the same main body so that, when the brush member is mounted to a driving rod, the brush member will be reciprocally turned to perform the tooth brushing and, when the nozzle member is mounted to the driving rod, water will be jetted out of the nozzle member to perform the gum cleaning and gum massaging.

A third object of the present invention is to provide a mouth cleaning device wherein the foregoing operations can be selectively made through a change-over switch.

A fourth object of the present invention is to provide a mouth cleaning device wherein a change-over switch can be automatically switched over by means of the brush and nozzle members.

Other objects of the present invention will be apparent by the following explanations with reference to the illustrated embodiments.

SUMMARY OF THE INVENTION

In the present invention, a driving means providing a reciprocal turning force to a brush member and a water feeding path which leads water from a water feeding means of a separate body to a nozzle member is built in a hollow case which is made to be a hand held gripping part of a mouth cleaning device, whereby the gripping part is minimized in size and the conventional problems are solved.

More particularly, in the mouth cleaning device according to the present invention a hollow case which forms a gripping part in the present invention is provided with an electric motor, a converting means which converts a rotary motion of said electric motor to a reciprocal turning motion, a driving rod reciprocally turned by said converting means, a water receiving port to which a hose connected to a water feeding means is connected and a water feeding path communicating with said water receiving port. The water feeding path is formed within the driving rod and a mount for a brush member and nozzle member is formed on said driving rod so that the brush and nozzle members can be interchangeably mounted.

Further in the present invention, a change-over switch for selectively changing over a source current feeding the driving device for the brush member and water feeding device for the nozzle member is selectively actuated by the mounting of the brush and nozzle members.

BRIEF DESCRIPTION OF THE DRAWINGS

The drawings show embodiments of the mouth cleaning device of the present invention, wherein:

FIGS. 18 to 22 illustrate another embodiment of the nozzle member in which

DETAILED DESCRIPTION OF THE INVENTION

Figure 6:
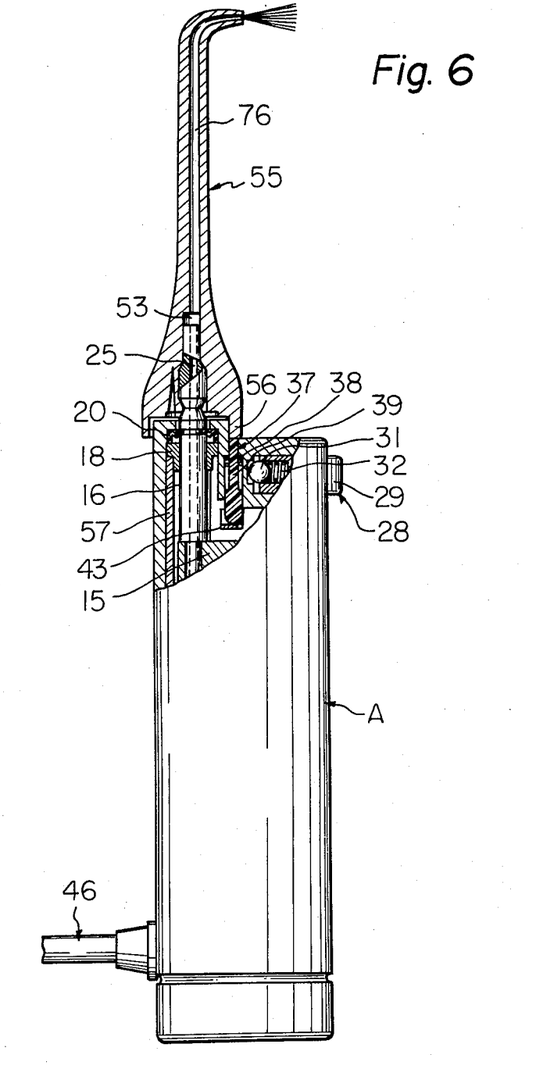
FIG. 6 shows a partly sectioned side view of the gripping part to which a nozzle member is mounted.
Figure 7:
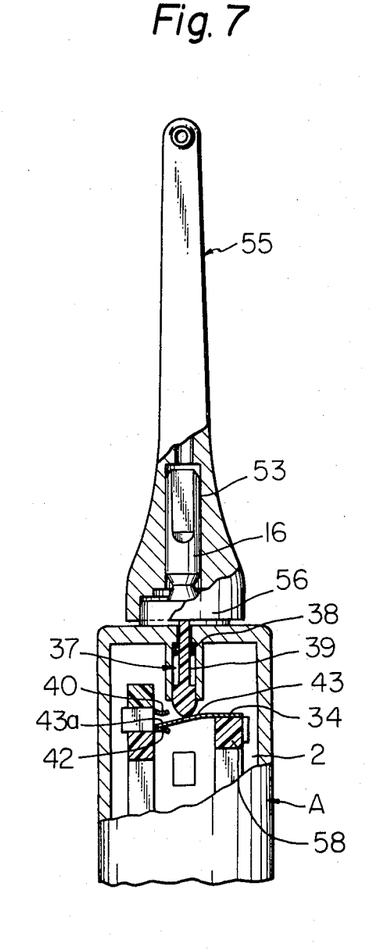
FIG. 7 shows a partly sectioned front view of the gripping part with the nozzle member mounted.

Explanations shall be made in the following with reference to the drawings showing embodiments of the present invention. In FIGS. 1 to 5, the mouth cleaning device has a hand held gripping part A. A hollow case 1 in which a driving unit inserting hole 2 is formed has at an upper end a driving rod passing hole 3 for a driving rod projection and a change-over pin sliding hole 4. The upper side surface of the case 1 has a switch sliding part 5 and the lower side surface has a receiving port 6 which penetrates through the case 1. An electric motor 7 is connected to an output shaft 8 to which a pinion 9 is fitted for rotations. The motor 7 is inserted in a motor fitting hole 11 formed in a base 10. A gear 12 having an eccentric pin 13 meshes with the pinion 9 which is borne on a shaft 14 formed on the upper surface of the base 10. A driving lever 15 provided at one end with a driving rod 16 and at the other end with a slot 17 which is formed to be long in the direction toward the driving rod 16. The eccentric pin 13 is engaged in this slot 17. A first bearing 18 is locked between the case 1 and the base 10. A second bearing 19 is fixed to the base 10, and the driving rod 16 having the driving lever 15 fixed in the intermediate part is supported at both ends. A first waterproof ring 20 is interposed between the passing hole 3 and the bearing 18 and a second waterproof ring 21 is interposed between the base 10 and the bearing 19. A converting means 22 is formed on the eccentric pin 13 and driving lever 15 so that the rotary motion of the motor 7 gives a reciprocal rocking motion of a fixed angle to the driving lever 15. This gives a reciprocal turning motion of a fixed angle to the driving rod 16 which is a center shaft of the reciprocal rocking motion of the driving lever 15. A water delivering part 23 formed in the base 10 parallel with the motor fitting hole 11 is provided with a thin partition wall 24 between it and the motor fitting hole 11. The water delivering part 23 is made to communicate with a water feeding path 25 by a connecting hole 26 formed in the base 10 which hole 26 is substantially of the same diameter as the water feeding path 25 and is considered so as to render the outer diameter of the case to be smaller. The water feeding path 25 and connecting hole 26 are thus formed to be substantially of the same diameter for the purpose of preventing an excess water pressure from being applied to a connecting part 27 of the base 10 with the driving rod 16 to thereby prevent water from leaking. Further, the bearing 19 and waterproof ring 21 are provided adjacent the connecting part 27 at the lower end of the driving rod 16 for the purpose of preventing the center of the driving rod 16 from being deviated to thereby prevent water from leaking out of the connecting part 27. A main switch 28 comprises a switch lever 29 operated with a finger, a steel ball 31 riding a projection 30 formed in the case 1 to achieve a click-stop of the switch lever 29, a spring 32 urging the steel ball 31 against the case 1, a switch cam 33 fitted to the lower end of the switch lever 29 for mounting this lever 29 to the case 1, a switch spring 35 supported at one end and urged by the switch cam 33 into contact with an anode plate 34 connecting the motor 7 to a current source for circuit opening and closing, and a third waterproof ring 36 for achieving a waterproofing between the case 1 and the switch cam 33. Thus, when the switch lever 29 mounted to the upper portion of the driving unit inserting hole 2 where the switch sliding hole 5 is formed is moved to its "ON" side along the periphery of the case 1, the switch cam 33 will press the switch spring 35 fitted above the base 10 so as to pass an electric current between the anode plate 34 and the current source. A change-over switch 37 comprises a change-over pin 39 formed to be stepped for fitting thereto a fourth waterproof ring 38, a terminal 40 connected to the motor 7, a terminal 42 connected to a water feeding means B through a relay 96 shown in FIG. 23, and the anode plate 34 of the foregoing main switch 28. A contact spring 43 formed to be tongue-shaped and integral with the anode plate 34. A movable contact 43a is formed at the free end. This contact spring 43 normally causes the change-over pin 39 which projects out of the change-over pin passing hole 4 to contact the terminal 40 provided in the base 10. When when the change-over pin 39 is depressed, the spring contacts the terminal 42 provided in the base 10 as opposed to the terminal 40. A driving unit 44 is formed of the base 10 and is housed in the driving unit inserting hole 2 of the case 1. A pipe-shaped water receiving port 45 formed in the side wall of the water delivering part 23 so as to connect thereto to a hose 46, as projected out of the receiving port 6. A fifth waterproof ring 47 is fitted to the port after the hose 46 is connected and a hose holder 48 formed of such elastic material as rubber or the like is fitted over the hose 46. A screw 49 which is screwed so that no water may leak out of the end part of the water delivering part 23. A lower cover 50 fitted to the driving unit inserting hole 2 through a sixth waterproof ring 51 and a spring 52 is provided in the lower cover 50 so as to press the motor 7 against the base 10. A mount 53 is formed on the outer periphery of projecting end of the driving rod 16 and a brush member 54 for brushing teeth or such nozzle member 55 for cleaning gums as in FIGS. 6 and 7 is mounted thereto so as to be prevented from slipping while rotating. In FIGS. 6 and 7, a change-over pin pressing part 56 is suspended from the lower end of the nozzle member 55 so as to depress the change-over pin 39 when the nozzle member 55 is mounted to the mount 53. Here, the change-over switch 37 may be a lead switch. An annular projection 57 is provided with a slit 57a on one side surface. The driving rod 16 is inserted into this annular projection 57 and the driving lever 15 is projected out of the slit 57a.

Figure 8:
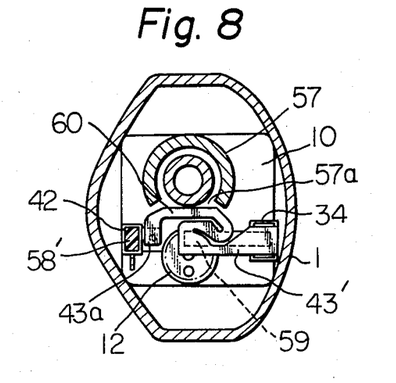
FIG. 8 shows a plan view of an essential part of another embodiment of a change-over switch provided in the gripping part of the foregoing.
Figure 9:
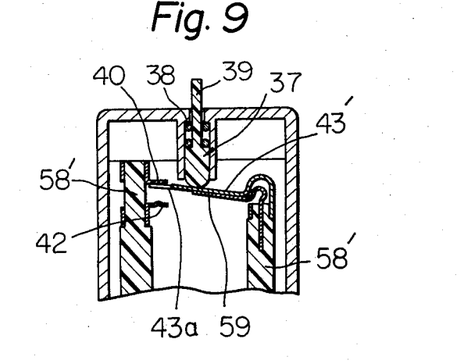
FIG. 9 shows a sectioned side view of the essential part of the change-over switch of FIG. 8.
Figure 10:
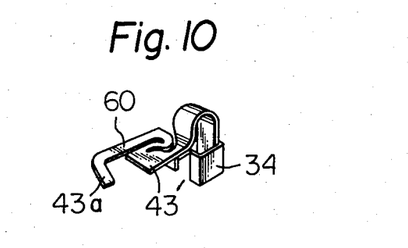
FIG. 10 shows a perspective view of a disassembled anode plate of the change-over switch.

Another embodiment of the change-over switch shall be explained next with reference to FIGS. 8 to 10. The contact spring 43' of the anode plate 34 is fixed at one end to a pillar-shaped projection 58' provided on the upper surface of the base 10 while the change-over pin 39 is engaged to the other end of the spring. An extension of the other end of the spring is turned in the same plane toward the fixed side and is formed in an S-shape as turned back again (see FIG. 10). There is provided a movable contact 43a at the tip of the extension. A supporting spring 59 supporting the contact spring 43 ensures a resetting of the change-over pin 39 and is provided so as to avoid contacting the turned-back part 60. Thus, the contact spring 43' can be displaced at the tip with a small load, any dimensional errors and assembling errors of the switch parts can be absorbed, the elastic fatigue of the contact spring whose spring force cannot be made stronger in relation to mounting and demounting force of the nozzle member 55 can be reduced and the reliability of the change-over switch can be elevated.

Figure 11:
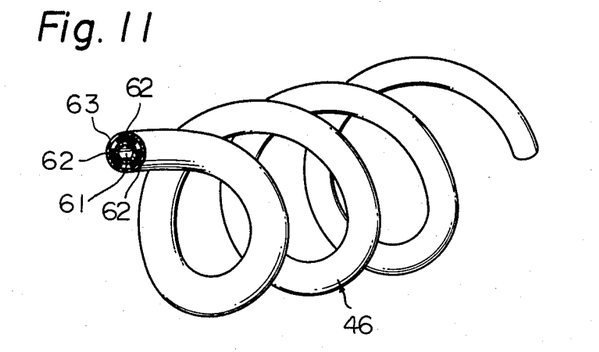
FIG. 11 shows a perspective view of a hose provided to the gripping part as sectioned at an end.
Figure 12:
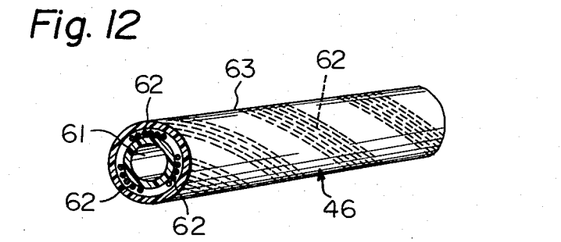
FIGS. 12 and 13 show perspective views of the foregoing hose as sectioned at an end.
Figure 13:
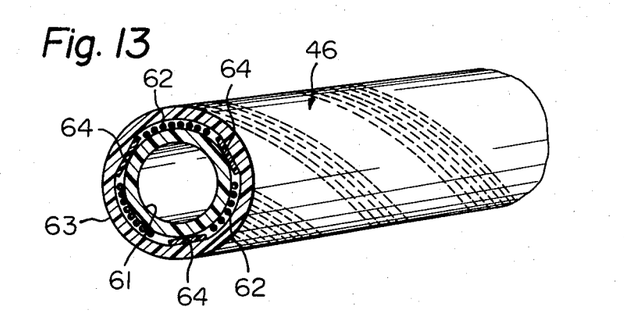
Figures 14, 15, 16:
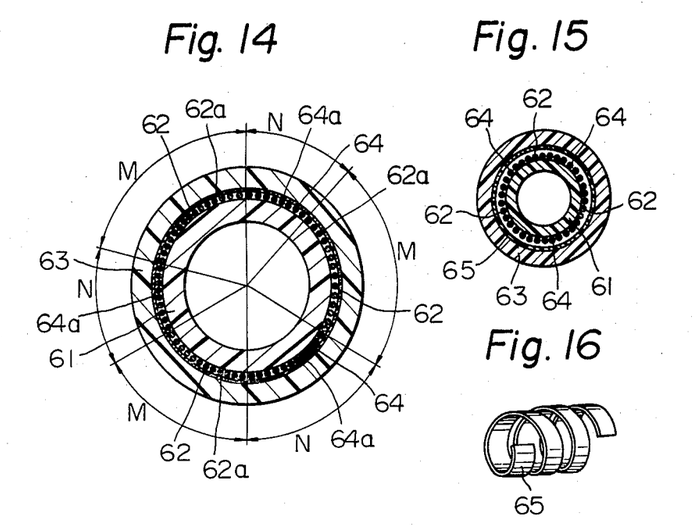
FIG. 14 shows a sectioned view of another embodiment of the hose.
FIG. 15 shows a sectioned view of a third embodiment of the hose.
FIG. 16 shows a perspective view of an insulating sheet to be used in the hose of FIG. 13.
Figure 17:
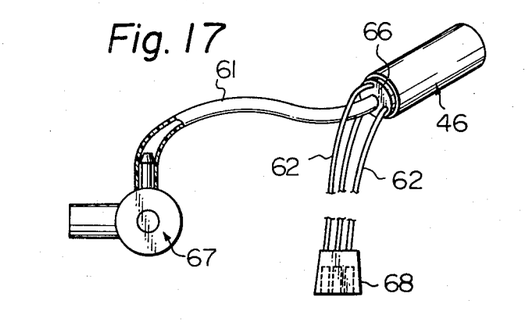
FIG. 17 shows a schematic perspective view of a manner of using the hose.

Now, the hose shall be explained with reference to FIGS. 11 to 17. In FIGS. 11 and 12, the hose 46 is formed of a hollow pipe 61 made of an electrically insulating material, a plurality of conductors 62 wound on the outer periphery of the pipe 61 and an outer coating 63 made of an electrically insulating material which covers the entire outer periphery of the pipe 61 over the conductors 62. The pipe 61 is formed of such synthetic resin as, for example, a high density polyethylene or the like, a plurality of copper wires coated with polyurethane is used for the conductors 62, and a composite material of vinyl chloride and rubber is used for the outer coating 63. In an embodiment shown in FIG. 12, there is shown an example wherein three sets of conductors 62 are helically wound over the entire longitudinal length on the outer periphery of the pipe 61 so as to be displaced by an angle of 120 degrees from each other in the peripheral direction in every cross-section of the hose 46, and the outer coating 63 is provided thereon over the entire longitudinal length. Such winding of the respective conductors 62 in a helical shape around the pipe 61 results in that, when the hose 46 is shaped to be a coil as curled, the respective conductors 62 will pass alternately outside and inside the coil and their length will be the same. When this coil is stretched, the respective conductors 62 will loosen in the part located outside the coil but will contract as tensioned in the part located inside the coil and tensile force applied to the conductors 62 inside the coil will be absorbed, whereby no unreasonable force will act on the respective conductors 62 and, as a result, the conductors 62 will be prevented from being broken. FIG. 13 shows another embodiment of the hose, wherein three strip-shaped electric insulators 64 molded of a polyethylene resin are wound on the outer periphery of the pipe 61 between the respective conductors 62 in the same manner as the conductors 62 so as to secure the insulating distance between the respective conductors 62 with the respective insulators 64, whereby, even if the hose 46 wound to be a coil as described above is repeatedly stretched and contracted, the respective conductors 62 will be positively prevented from being displaced to contract. In a further embodiment shown in FIG. 14, a plurality of polyethylene filaments 64a substantially of the same diameter as of the copper wires 62a forming the conductors 62 are wound side by side in the peripheral direction of the pipe 61 to form a set of electric insulators 64. The conductors 62 are disposed in the ranges indicated by M in the drawing while the electric insulators 64 are disposed in the ranges indicated by N. The copper wires 62a and filaments 64a of the same diameter are arranged in arrays on the outer periphery of the pipe 61, so that their fitness to the outer coating 63 will be excellent without pushing up the coating 63. In this way, the outer surface of the outer coating 63 can be finished to be of a smooth surface having no irregularities, and the hose can be made to have not only a good apperance but also a high degree of affinity in the case of connecting the hose 46 to the water receiving port 45 or the like of the mouth cleaning device. In FIG. 15, there is shown an example in which an insulating sheet 65 made of such strip-shaped polyester sheet as shown in FIG. 16 is wound over the entire periphery on an annulus 61 formed of the conductors 62 and insulators 64. The insulating sheet 65 is further covered wth the outer coating 63, so that the outer coating 63 will not bite into the conductors 62 and electric insulators 64. The outer coating 63 can be easily peeled off in the case of exposing the respective conductor wires 62 out of the end of the hose 46 and the conductors 62 will be positively prevented from being hurt by mistake. At an end of the hose 46, as shown in FIG. 17, a separator 66 made of a synthetic resin which is an electric insulating material is attached. The the pipe 61 and respective conductors 62 are separately led out of the hose 46 to be connected respectively to such corresponding members as, for example, a pump 67 and connector 68 as shown in the drawing.

Figure 18:
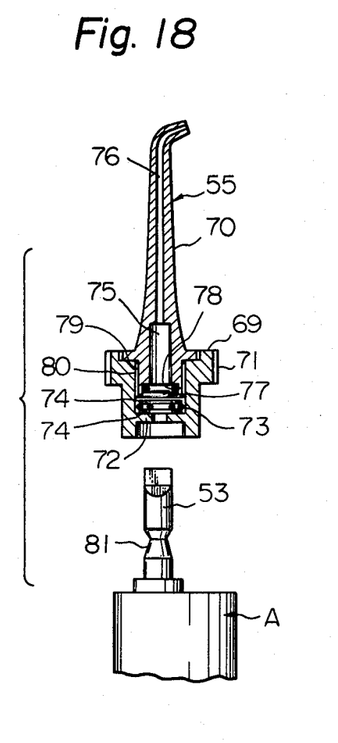
FIG. 18 shows a sectioned view of the nozzle member as demounted from the gripping part.
Figure 19:
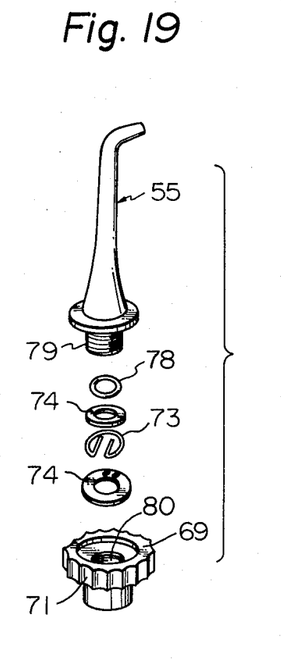
FIG. 19 shows a perspective view of a disassembled nozzle member and gripping part.
Figure 20:
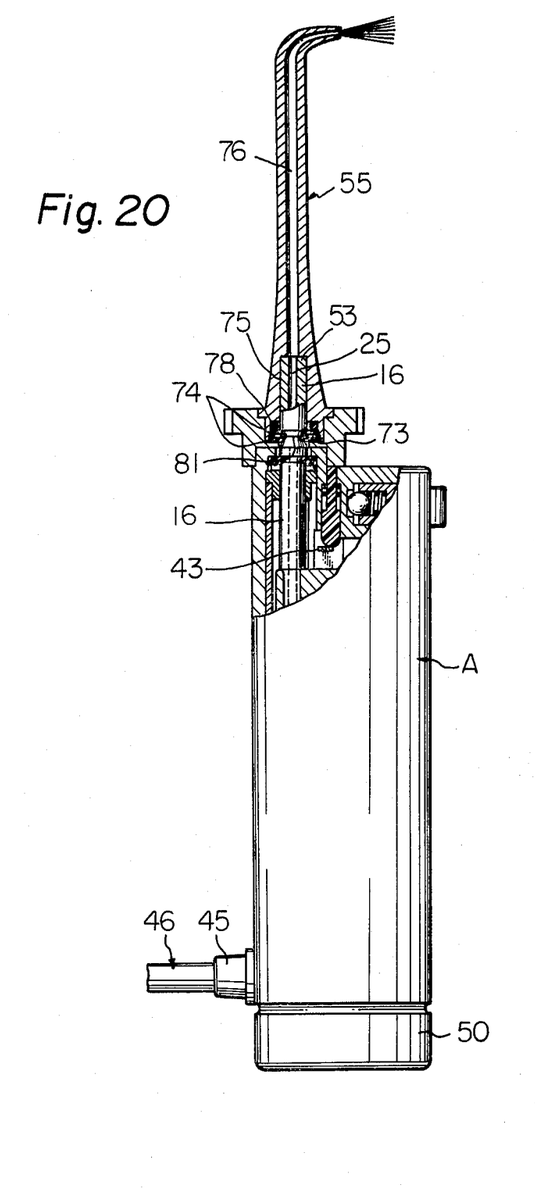
FIG. 20 shows a vertically sectioned view of the foregoing nozzle member mounted to the gripping part.
Figure 21:
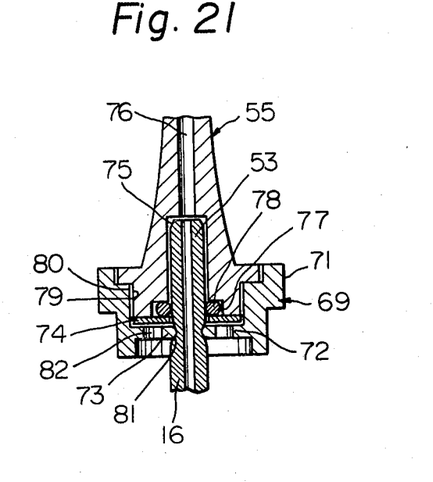
FIG. 21 shows a sectioned view of another embodiment of the nozzle body and FIG. 22 shows a perspective view of the foregoing nozzle member as disassembled.
Figure 22:
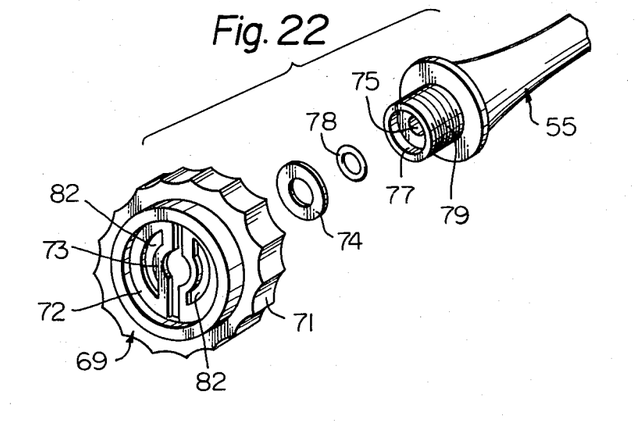

Next, another embodiment of the nozzle member holding means shall be explained with reference to FIGS. 18 to 20. The nozzle member 55 is formed of a tubular nozzle grip 69 and a nozzle 70. The nozzle grip 69 has nonskid concaves 71 on the outer periphery and a resilient locking member 73 formed of a wire spring material is set in a stepped part 72 formed within the nozzle grip 69. Rings 74 are positioned respectively above and below the resilient locking member 73. An output shaft inserting hole 75 is provided in the lower part of the nozzle 70. This inserting hole 75 communicates with a hole 76 and an O-ring 78 is fitted in a large diameter part 77 of the lower opening. A male screw part 79 on the lower outer peripheral part of the nozzle 70 is screwed into a female screw part 80 of the nozzle grip 69 to mount the nozzle grip 69 to the lower part of the nozzle 70. A locking recess 81 is formed in the mount 53 of the driving rod 16. In mounting the nozzle member 55 to the mount 53 of the driving rod 16, the driving rod 16 is inserted into the nozzle grip 69, the resilient locking member 73 is locked in the locking recess 81, the mount 53 is inserted at its tip into the output shaft inserting hole 75 in the lower part of the nozzle 70 and the watertightness between the mount 53 of the driving rod 16 and the lower surface part of the nozzle 55 is maintained by means of the O-ring 78. FIGS. 21 and 22 show another embodiment of the nozzle-member holding means wherein a substantially circular resilient locking member 73 is formed of a synthetic resin integrally with the nozzle grip 69. The central part of the locking member 73 is provided with a stepped part 72 within the nozzle grip 69. Cut-through holes 82 are formed in the stepped part 72 so as to give a resiliency to the resilient locking member 73. The mount 53 of the driving rod 16 is inserted into the nozzle grip 69 to engage the resilient locking member 73 in the locking recess 81. The tip part of the driving rod 16 is inserted into the output shaft inserting hole 75 in the lower part of the nozzle member 55. The watertightness between the driving rod 16 and the lower surface part of the nozzle member 55 is kept by the O-ring 78 so that, in holding the nozzle member 55 on the driving rod 16, the resilient locking member 73 made of a spring material is made to have a holding function. As the sealing of the nozzle member 55 and driving rod 16 is performed by the O-ring 78, the O-ring 78 can be made to have only a sealing function, the O-ring 78 is less worn even when the mounting and demounting are repeated and the sealing is so positive that no water is caused to leak. Such advantages are remarkable in a type in which a push-up force due to the contact spring 43 is always incurred and, as an inserting system is adopted for mounting the nozzle member 55 to the driving rod 16, its mounting and demounting are made easier.

Figure 23:
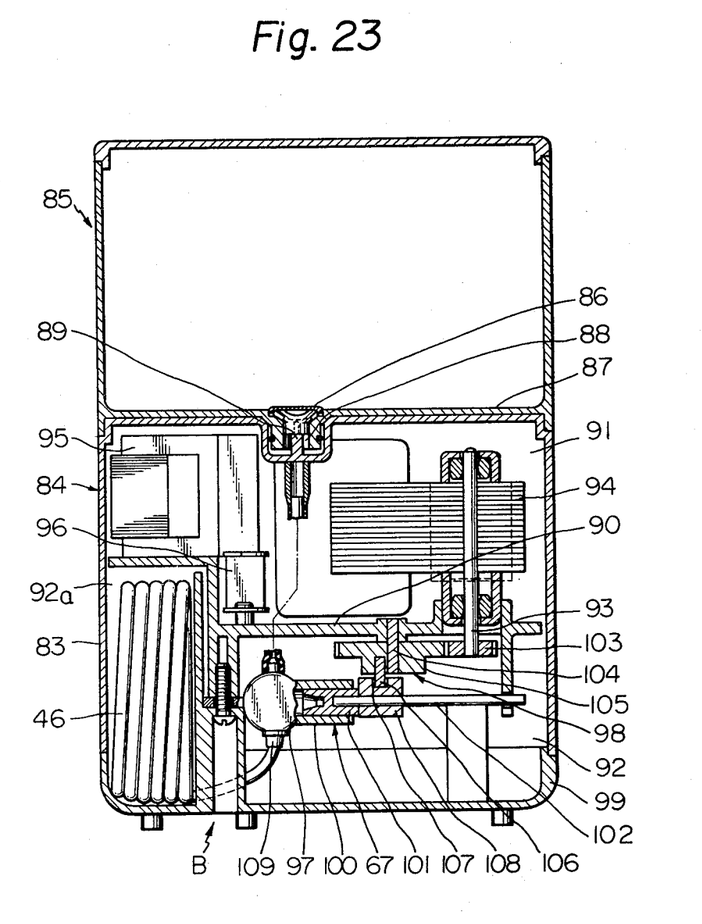
FIG. 23 shows a vertically sectioned view of a water feeding means.
Figure 24:
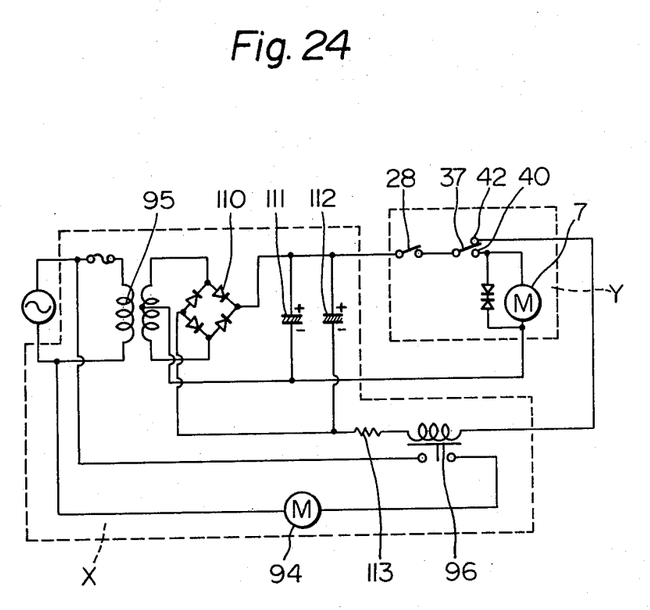
FIG. 24 is an electric circuit diagram for the present invention.

Next, the water feeding means B shall be explained with reference to FIG. 23. A housing case 83 is divided into an upper part and a lower part which are an upper case 84 and lower case 99 for housing the water feeding means. A container 85 is removably provided on the upper case 84. A plug 86 for opening and closing a water flowing hole 88 is formed in the bottom 87 of the container 85 so that, when the container 85 is removed from the housing case 83, the water flowing hole 88 will be closed by the plug 86. When the container 85 is fitted to the housing case 83, the plug 86 will be pushed up by a projection 89 provided on the upper surface of the housing case 83, the water flowing hole 88 will be opened and water contained in the container will be fed to the pump 67. Further, the housing case 83 is divided by a partition wall 90 into an upper part of an electric chamber 91 and a lower part of a pump chamber 92 so that no problem of electric shock due to water leaking will arise. A housing part 92a is for the gripping part A. In the electric chamber 91, there are provided an electric motor 94 for the pump having an output shaft 93 projected into the pump chamber 92, a voltage reducing transformer 95 for feeding an electric current as reduced in the voltage to the motor 7 provided in the gripping part A and a relay 96 operated by the change-over switch 37 to stop one of the motors 7 and 94, the latter being for the pump, but to operate the other motor. In the pump chamber 92, the pump 67 formed of a cylinder block 97 and a transmission unit 98 is housed. The cylinder block 97 is formed of a hollow cylinder 100 held between the lower case 99 and partition wall 90, a piston 101 reciprocally sliding within the cylinder 100 and a piston rod 102 extended from this piston 101 and held at an end by the partition wall 90. The transmission unit 98 is formed of a gear 103 secured to the output shaft 93, a gear 105 borne on a shaft 104 of the partition wall 90 as meshed with the gear 103, an eccentric pin 106 formed on the gear 105 and a supporter 108 having an elongated groove 107 formed to be long in the direction perpendicular to the reciprocating direction of the piston 101. The transmission unit 98 reciprocates the piston 101 in one direction as engaged with the eccentric pin 106, and the piston rod 102 is fixed to the supporter 108. When the rotary motion of the motor 94 for the pump is converted to a reciprocating motion of the piston 101 by the transmission unit 98 and water is fed to the pump 67, water of an intermittent pulsating flow will be jetted to the gripping part A through the hose 46 out of a delivery port 109 of the pump 67. FIG. 24 is a circuit diagram showing electric wirings relating to the operation of the pump 67 of the water feeding means B and the operation of the brush member 54 or nozzle member 55 of the gripping part A. The main switch 28 and smoothing capacitors 111 and 112 are connected through a rectifier 110 to the secondary side of the voltage reducing transformer 95, and the other terminal of the secondary side of the voltage reducing transformer 95 is connected to the cathode of the motor 7 and the smoothing capacitor 111. The anode of the motor 7 is connected to a terminal of the main switch 28 through the terminal 40 of the change-over switch 37. The terminal 42 of the change-over switch 37 and the cathode of the motor 7 are connected through a current passing coil of the relay 96 and a resistance 113. The relay 96 is connected with the motor 94 for the pump connected to the primary terminal of the transformer 95 through a contact terminal of this relay 96. A circuit part X is on the side of the water feeding means B, and a circuit part Y is on the side of the gripping part A.

Figure 1:
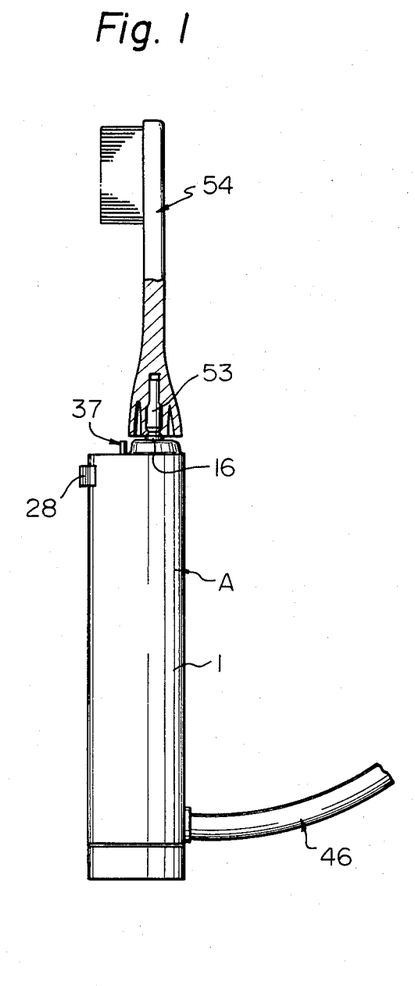
FIG. 1 shows a partly sectioned side view of a gripping part to which a brush member is mounted.
Figure 2:
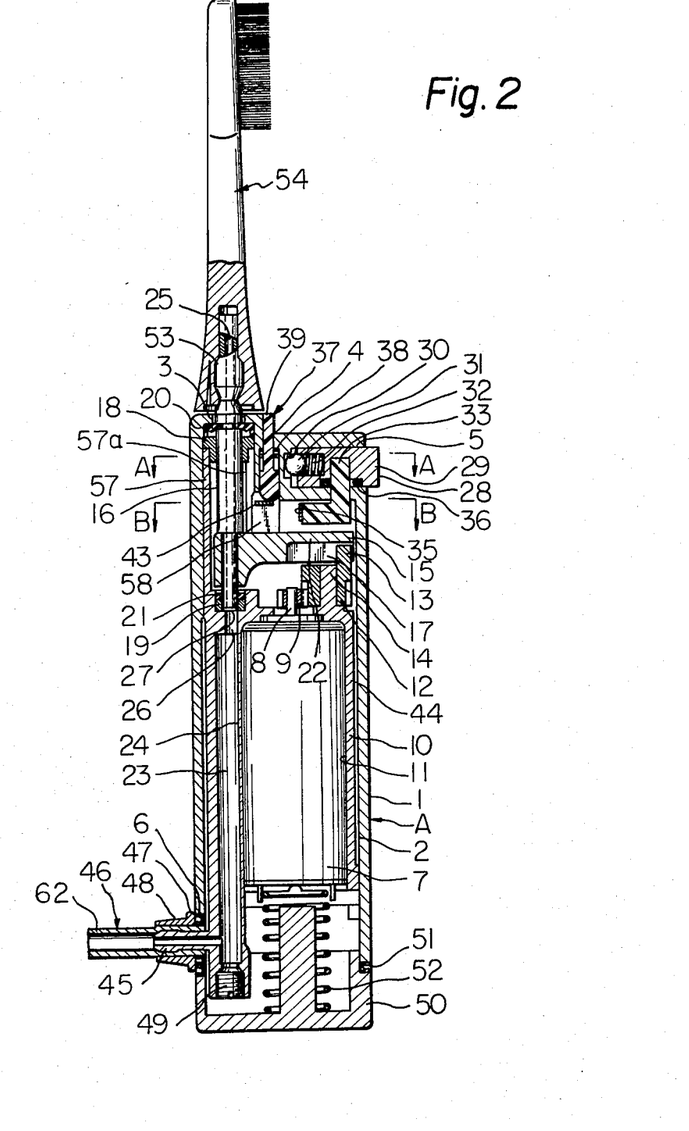
FIG. 2 shows a vertically sectioned view of the gripping part to which the brush member is mounted.
Figures 3, 4, 5:
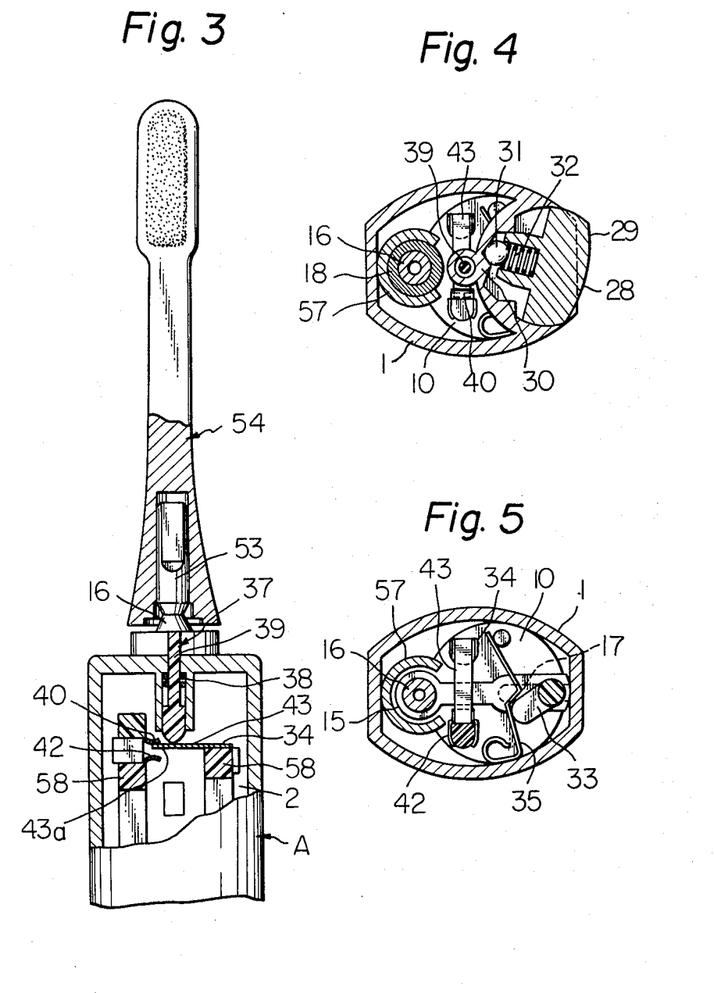
FIG. 3 shows a partly sectioned front view of the gripping part to which the brush member is mounted.
FIG. 4 shows a sectioned view of A—A in FIG. 2.
FIG. 5 shows a sectioned view on B—B in FIG. 2.

The operation of the mouth cleaning device will now be described. As shown in FIGS. 2 and 3 when the gripping part A of the mouth cleaning device is pulled out drawing the hose 46 in the coil shape and the brush member 54 is mounted to the mount 53 of the driving rod 16, the contact spring 43 will be in contact with the terminal connected to the motor 7. When the main switch 28 is turned ON, the motor 7 will be operated, the driving rod 16 will be reciprocally turned on and the brush member 54 will be reciprocally turned to brush teeth. When the brush member 54 is demounted and the nozzle member 55 is mounted to the mount 53 of the driving rod 16, the change-over pin 39 will be pressed downward by the change-over pin pressing part 56. As in FIGS. 6 and 7, the contact spring 43 of the change-over switch 37 will contact the terminal 42 connected through the conductors 62 to the relay 96 in the water feeding means B. The relay 96 will operate and the motor 94 for the pump will be operated by this relay 96 to feed water to the water receiving port 45. This water will be fed to the nozzle member 55 through the water delivering part 23 and the water feeding path 25 within the driving rod 16 to perform the gum cleaning and massage. When the hand pulling the gripping part A is released, the hose 46 will return to be housed in the housing part 92a.

Thus, in the mouth cleaning device to which the present invention relates, the motor 7 for reciprocally turning the brush member 54 and the converting means 22 are provided in the hollow case 1 and water to be jetted out of the nozzle member 55 is fed from the separate water feeding means B so as to be jetted out of the nozzle member 55 through the pierced through driving rod 16. The effects are that the brush member 54 for brushing teeth and the nozzle member 55 for cleaning gums can be interchangeably used with respect to a single gripping part A, yet a mouth cleaning device compact and easy to use can be provided. Further, the brush member 54 can be driven even without water in the water feeding means as compared with the conventional mouth cleaning device wherein the brush member 54 is driven by a hydraulically operated motor.

We claim:

1. A mouth cleaning device, comprising:
    a hollow case which forms a hand held gripping part and which has an electric motor therein;
    a converting means for converting rotary motion of said motor to a reciprocal turning motion;
    a driving rod reciprocally turned by said converting means;
    a water receiving port having a hose connected to a water feeding means;
    a first water feeding path communicating with said water receiving port;
    a second water feeding path being formed within said driving rod and communicating with said first water feeding path;
    a mount for selectively receiving a brush member and a nozzle member being formed on said driving rod, said brush and nozzle members being interchangeably mounted; and
    a change-over switch for selectively actuating said motor when said brush member is mounted to said driving rod and actuating said water feeding means when said nozzle member is mounted to the driving rod.

2. A mouth cleaning device as recited in claim 1 wherein said brush member and said nozzle member each include means for automatically switching said change-over switch in response to the respective mounting of said brush member and said nozzle member to the driving rod.

3. A mouth cleaning device according to claim 2 wherein said change-over switch comprises a contact spring holding its movable contact, a fixed terminal, and a change-over pin for transmitting an operating force to said contact spring, said change-over pin being depressed by a mounting of said nozzle member to actuate said change-over switch.

4. A mouth cleaning device according to claim 3 wherein said contact spring is reinforced by another supporting spring from its fixing base to a portion adjacent abutting position of said change-over pin.

5. A mouth cleaning device according to claim 3 wherein, in said change-over switch, said contact spring fixed at one end is formed in an extension at the other end to be an S-shape as turned to said fixed end side in a plane and further turned once again, and a movable contact is provided at the tip of said extension.

6. A mouth cleaning device as recited in claim 1 wherein said hose is helically shaped and formed of an electrically insulating material defining a peripheral wall of said hose and a plurality of sets of helically wound conductors embedded within said peripheral wall, said conductors being separated from each other over the entire longitudinal length of said hose, and said conductors being electrically interconnected between said water feeding means and said switch for conducting electrical current therebetween.

* * * * *